(12) United States Patent
Song et al.

(10) Patent No.: US 12,325,751 B2
(45) Date of Patent: Jun. 10, 2025

(54) ANTI-CD25 ANTIBODY AND APPLICATION THEREOF

(71) Applicant: Shandong Boan Biotechnology Co., Ltd., Shandong (CN)

(72) Inventors: Deyong Song, Shandong (CN); Xiu Liu, Shandong (CN); Jing Han, Shandong (CN)

(73) Assignee: Shandong Boan Biotechnology Co., Ltd., Yantai (CN)

( * ) Notice: Subject to any disclaimer, the term of this patent is extended or adjusted under 35 U.S.C. 154(b) by 920 days.

(21) Appl. No.: 17/601,321

(22) PCT Filed: Jun. 8, 2020

(86) PCT No.: PCT/CN2020/094919
§ 371 (c)(1),
(2) Date: Oct. 4, 2021

(87) PCT Pub. No.: WO2020/248938
PCT Pub. Date: Dec. 17, 2020

(65) Prior Publication Data
US 2022/0195055 A1  Jun. 23, 2022

(30) Foreign Application Priority Data

Jun. 10, 2019 (CN) .......................... 201910495614.4
Jun. 10, 2019 (CN) .......................... 201910495626.7

(51) Int. Cl.
| | | |
|---|---|---|
| A61K 39/395 | (2006.01) | |
| C07K 16/28 | (2006.01) | |
| C12N 15/13 | (2006.01) | |
| G01N 33/574 | (2006.01) | |
| G01N 33/577 | (2006.01) | |

(52) U.S. Cl.
CPC ....... *C07K 16/2866* (2013.01); *G01N 33/574* (2013.01); *G01N 33/577* (2013.01); *C07K 2317/55* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | |
|---|---|---|
| 6,521,230 B1 | 2/2003 | Amlot et al. |
| 2004/0170626 A1 | 9/2004 | Schuurman et al. |
| 2008/0317746 A1 | 12/2008 | Bauerle et al. |
| 2020/0010554 A1 | 1/2020 | Goubier et al. |
| 2020/0140538 A1 | 5/2020 | Surh et al. |

FOREIGN PATENT DOCUMENTS

| | | |
|---|---|---|
| CN | 103571872 | 11/2016 |
| WO | WO 2004045512 | 6/2004 |
| WO | WO 2018167104 | 9/2018 |
| WO | WO 2020248938 | 12/2020 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Research Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Extended European Search Report in European Appln. No. 20822215.8, dated May 31, 2022, 9 pages.
International Preliminary Report on Patentability in International Appln. No. PCT/CN2020/094919, dated Dec. 14, 2021, 12 pages (with English Translation).
International Search Report and Written Opinion in International Appln. No. PCT/CN2020/094919, dated Sep. 14, 2020, 10 pages (with English Translation).
Martin, "Humanized anti-CD25 antibody treatment with daclizumab in multiple sclerosis," Neurodegenerative Dis, 2008 5(1):23-26.
Onishi et al., "Immunotherapy approaches targeting regulatory T-cells," Anticancer Res, Mar. 2012, 32(3):997-1003.
Rubin et al., "A monoclonal antibody 7G7/B6, binds to an epitope on the human interleukin-2 (IL-2) receptor that is distinct from that recognized by IL-2 or anti-Tac," Hybridoma, Jan. 1985, 4(2):91-102.

(Continued)

*Primary Examiner* — Christine J Saoud
*Assistant Examiner* — Jon M Lockard
(74) *Attorney, Agent, or Firm* — Fish & Richardson P.C.

(57) ABSTRACT

The present invention provides an antibody binding to CD25 or an antigen-binding fragment thereof and a use thereof for the preparation of a therapeutic cancer drug. The antibody or antigen-binding fragment thereof comprises a light chain variable region and a heavy chain variable region containing a specific complementarity-determining region sequence. The antibody or antigen-binding fragment has one or more of the following advantages: enhanced CD25 protein binding ability, enhanced CD25 protein affinity, enhanced CD25 expressing cell killing ability, weakened PBMC activation inhibition, enhanced in vivo tumor growth inhibition ability, enhanced in vivo tumor killing ability, enhanced ability to reduce the number of Treg cells, or enhanced ability to increase the number of effector T cells.

14 Claims, 5 Drawing Sheets
Specification includes a Sequence Listing.

(56) References Cited

OTHER PUBLICATIONS

Shang et al., "Prognostic value of tumor-infiltrating FoxP3+ regulatory T cells in cancers: a systematic review and meta-analysis," Scientific Reports, Oct. 2015, 5:15179, 9 pages.

Tanaka et al., "New monoclonal antibodies that define multiple epitopes and a human-specific marker on the interleukin 2 receptor molecules of primates," Microbiology and Immunology, Apr. 1986, 30(4):373-388.

Walker et al., "Pharmacokinetic comparison of a diverse panel of non-targeting human antibodies as matched IgG1 and IgG2 isotypes in rodents and non-human primates," PLoS One, May 2019, 14(5):e0217061, 24 pages.

\* cited by examiner

ANTI-CD25 ANTIBODY AND APPLICATION THEREOF

CROSS-REFERENCE TO RELATED APPLICATIONS

This application is a National Stage Application under 35 U.S.C. § 371 of International Application No. PCT/CN2020/094919, filed on Jun. 8, 2020, which claims priority to Chinese Application No. 201910495626.7, filed on Jun. 10, 2019, and Chinese Application No. 201910495614.4, filed on Jun. 10, 2019, the contents of which are incorporated herein by reference in their entirety.

TECHNICAL FIELD

The invention generally relates to a biomedical field, and more specifically, to an antibody that binds to CD25 and the application thereof.

BACKGROUND

Regulatory T cells (Treg) play a vital role in mediating immune homeostasis, and can promote the establishment and maintenance of peripheral tolerance. However, their role becomes more complex in the context of cancer. Because cancer cells express their own tumor-associated antigens, the presence of Treg that suppresses the response of effector cells can promote tumor progression. Therefore, the infiltration of Treg in established tumors is one of major obstacles for efficacy. Treg that uses inhibitory mechanisms is believed to make a significant contribution to the limitations and even failures of current therapies, especially immunotherapies that rely on inducing or enhancing anti-tumor responses (Onishi H et al., 2012 Anticanc. Res. 32, 997-1003). The tumor infiltration of Treg is also associated with several human cancers with poor prognosis (Shang B et al., 2015, Sci Rep. 5:15179). It has been proven that Treg cells contribute to the establishment and progression of tumors in mouse models and their absence leads to a delay in tumor progression. In humans, a high proportion of the infiltration of tumor Treg cells, more importantly, a lower ratio of effector T cells (Teff) to Treg cells, is associated with the poor prognosis of various human cancers (Shang et al., 2015).

CD25 is one of the potential molecular targets to achieve Treg depletion. CD25 is also known as interleukin-2 high affinity receptor alpha chain (IL-2Rα). CD25 is expressed at high levels on Treg, but CD25 is not present or expressed at low levels on Teff.

In the prior art, there are antibodies that bind to CD25 but do not block the binding of IL2 to CD25, such as MA251 (Rubin et al., 1985, Hybridoma 4(2)91-102, Tanaka et al., 1986, Microbiol. Immunol 30(4), 373-388), but they still exist defects such as insufficient CD25 binding activity, inhibition of PBMC activation, and general pharmacokinetic performance.

In the face of the patient's demand for medicines for disease treatment, especially demands for antibody drugs, there is still an urgent clinical need to provide an anti-CD25 antibody with higher binding activity.

SUMMARY

In the full text of the present invention, various embodiments regarding VL (light chain variable region), VH (heavy chain variable region), LCDR (light chain complementarity determining region), HCDR (heavy chain complementarity determining region), LCDR1, LCDR2, LCDR3, HCDR1, HCDR2 and HCDR3 may be implemented individually or in any combination.

In an aspect of the present invention, the present invention relates to an antibody or antigen-binding fragment thereof including three heavy chain complementarity determining regions, wherein the HCDR1 amino acid sequence is represented by SEQ ID NO: 14, the HCDR2 amino acid sequence is represented by SEQ ID NO: 15, and the HCDR3 amino acid sequence is represented by SEQ ID NO: 16. Further, the antibody or antigen-binding fragment thereof further includes three light chain complementarity determining regions, wherein the LCDR1 amino acid sequence is represented by SEQ ID NO: 11, the LCDR2 amino acid sequence is represented by SEQ ID NO: 12, and the LCDR3 amino acid sequence is represented by SEQ ID NO: 13.

In an aspect of the present invention, the antibody or antigen-binding fragment thereof provided in the present invention includes a heavy chain variable region represented by SEQ ID NO: 4; preferably, further includes a light chain variable region represented by SEQ ID NO: 3.

In an aspect of the present invention, the present invention relates to an antibody or antigen-binding fragment thereof including three light chain complementarity determining regions, wherein the LCDR1 amino acid sequence is represented by SEQ ID NO: 5, the LCDR2 amino acid sequence is represented by SEQ ID NO: 6, and the LCDR3 amino acid sequence is represented by SEQ ID NO: 7; and/or three heavy chain complementarity determining regions, wherein the HCDR1 amino acid sequence is represented by SEQ ID NO: 8, the HCDR2 amino acid sequence is represented by SEQ ID NO: 9, and the HCDR3 amino acid sequence is represented by SEQ ID NO: 10.

In another aspect, the present invention relates to an antibody or antigen-binding fragment thereof including the light chain variable region of the amino acid sequence represented by SEQ ID NO: 1, and/or the heavy chain variable region of the amino acid sequence represented by SEQ ID NO: 2.

According to an aspect of the present invention, the sequence of the light chain constant region of the antibody or antigen-binding fragment thereof of anyone of the preceding aspects is SEQ ID NO: 20.

According to an aspect of the present invention, the sequence of the heavy chain constant region of the antibody or antigen-binding fragment thereof of any one of the preceding aspects is SEQ ID NO: 17.

Specifically, the antibody or antigen-binding fragment thereof provided in the present invention preferably includes the light chain variable region of the amino acid sequence represented by SEQ ID NO: 3, the heavy chain variable region of the amino acid sequence represented by SEQ ID NO: 4, the light chain constant region of the amino acid sequence represented by SEQ ID NO: 20 and the heavy chain constant region of the amino acid sequence represented by SEQ ID NO: 17.

Specifically, the antibody or antigen-binding fragment thereof provided in the present invention preferably includes the light chain variable region of the amino acid sequence represented by SEQ ID NO: 1, the heavy chain variable region of the amino acid sequence represented by SEQ ID NO: 2, the light chain constant region of the amino acid sequence represented by SEQ ID NO: 20 and the heavy chain constant region of the amino acid sequence represented by SEQ ID NO: 17.

According to an aspect of the present invention, the antibody or antigen-binding fragment thereof of the present invention binds to CD25, preferably to human CD25.

According to an aspect of the present invention, the present invention relates to the antibody or antigen-binding fragment thereof of any one of the preceding aspects including a monoclonal antibody, a polyclonal antibody, a chimeric antibody, a humanized antibody, a Fab fragment, a Fab' fragment, a F(ab')2 fragment, a Fv fragment, a scFv fragment, a dsFv fragment or the like.

According to an aspect of the present invention, the present invention relates to a nucleic acid encoding the antibody or antigen-binding fragment thereof of any one of the preceding aspects.

According to an aspect of the present invention, the present invention relates to a vector including the nucleic acid of the preceding aspect, or the vector can express the antibody or antigen-binding fragment thereof of anyone of the preceding aspects. Preferably, the vector may be a viral vector; preferably, the viral vector includes but is not limited to a lentiviral vector, an adenovirus vector, an adeno-associated viral vector, a retroviral vector, or the like; preferably, the vector may be a non-viral vector; preferably, the vector may be a mammalian cell expression vector; preferably, the expression vector may be a bacterial expression vector; and preferably, the expression vector may be a fungal expression vector.

According to an aspect of the present invention, the present invention relates to a cell that can express a cell of the antibody or antigen-binding fragment thereof of any one of the preceding aspects. Preferably the cell is a bacterial cell; preferably the bacterial cell is an *E. coli* cell and the like; preferably the cell is a fungal cell; preferably the fungal cell is a yeast cell; preferably the yeast cell is a *Pichia pastoris* cell and the like; preferably the cell is a mammalian cell; preferably the mammalian cell is a Chinese hamster ovary cell (CHO), a human embryonic kidney cell (293), a B cell, a T cell, a DC cell, a NK cell, or the like.

According to an aspect of the present invention, the present invention relates to a pharmaceutical composition including the antibody or antigen-binding fragment thereof, the nucleic acid, the vector or the cell of anyone of the preceding aspects, preferably the pharmaceutical composition further includes a pharmaceutically acceptable excipient, and the pharmaceutically acceptable vector preferably includes one or more of the following: a solvent, a dispersant, an additive, a plasticizer and the like which are pharmaceutically acceptable.

In some embodiments, the pharmaceutical composition may further include other therapeutic agents. In some embodiments, the other therapeutic agents include chemotherapeutic agents, immunotherapeutic agents, or hormonal therapeutic agents. The combined administration of the antibody or antigen-binding fragment thereof and the other therapeutic agents can enhance the therapeutic effect of the therapeutic agents.

In some embodiments, the "enhance the therapeutic effect" refers to enhancing the therapeutic effect of other therapeutic agents or therapies. The antibody or antigen-binding fragment provided in the present invention can be administered individually or in combination with other therapeutic agents or therapies. In some embodiments, the other therapeutic agents or therapies include chemotherapeutic agents, immunotherapeutic agents, hormonal therapeutic agents, radiation therapy and surgery.

According to an aspect of the present invention, there is provided a kit including the antibody or antigen-binding fragment thereof of the present invention, or including a nucleic acid encoding the antibody or antigen-binding fragment thereof.

According to an aspect of the present invention, the present invention relates to an application of the antibody or antigen-binding fragment thereof, the nucleic acid, the vector or the cell of any one of the preceding aspects in preparation of medicaments for treatment or prophylaxis of diseases.

According to an aspect of the present invention, the present invention relates to an application of the antibody or antigen-binding fragment thereof or the nucleic acid of any one of the preceding aspects in preparation of diagnostic or detection kits.

In an aspect of the present invention, there is provided a method of treating or preventing diseases including administering the antibody or antigen-binding fragment thereof, the nucleic acid, the vector, the cell or the pharmaceutical composition of the present invention to subjects in need.

In an aspect of the present invention, there is provided a method of diagnosis or detection including administering the antibody or antigen-binding fragment, the nucleic acid or the kits of the present invention to subjects or samples in need. Preferably, the method is a method of diagnosing or detecting diseases.

According to an aspect of the present invention, the present invention relates to use of the antibody or antigen-binding fragment thereof, the nucleic acid, the vector, the cell or the pharmaceutical composition of any one of the preceding aspects for the treatment or prophylaxis of diseases.

According to an aspect of the present invention, the present invention relates to use of the antibody or antigen-binding fragment thereof, the nucleic acid, or the kits of any one of the preceding aspects for detection or diagnosis. Preferably, the use is to diagnose or detect diseases.

According to an aspect of the present invention, the disease is a cancer.

According to an aspect of the present invention, the cancer includes gastric cancer, esophageal cancer, head-and-neck cancer, bladder cancer, cervical cancer, sarcoma, cytoma, lung cancer, colon cancer, ovarian cancer, renal cancer, colorectal cancer, pancreatic cancer, liver cancer, melanoma, breast cancer, myeloma, glioma, leukemia, lymphoma and the like.

According to an aspect of the present invention, the present invention relates to a method for preparing the antibody or antigen-binding fragment thereof of any one of the preceding aspects, which includes transfecting cells with the above vector, and expressing the antibody or antigen-binding fragment thereof by the transfected cells; or includes expressing the antibody or antigen-binding fragment thereof with the above cell.

According to an aspect of the present invention, the antibody or antigen-binding fragment thereof provided in the present invention has one or more of the following advantages: enhanced CD25 protein binding activity, enhanced CD25 protein affinity, enhanced CD25 expressing cell killing ability, reduced PBMC activation inhibition, enhanced in vivo tumor growth inhibition ability, enhanced in vivo tumor killing ability, enhanced ability to reduce the number of Treg cells, or enhanced ability to increase the number of effector T cells.

BRIEF DESCRIPTION OF THE DRAWINGS

In order to more clearly explain the specific embodiments of the present invention or the technical solutions in the prior art, the drawings required for the specific embodiments or the description of the prior art will be briefly described below. Obviously, the drawings in the follow description are some embodiments of the present invention, and those of ordinary skill in the art can obtain other drawings based on these drawings without the exercise of inventive faculty.

FIG. 7A to FIG. 7B show the efficacy results of the candidate antibodies in B-hIL2Rα humanized mouse MC38 colon cancer animal model in Example 5.1, wherein FIG. 7A shows the body weight data of MC38 tumor model mice, and FIG. 7B shows the tumor volume data of the MC38 tumor model.

DESCRIPTION

The technical solutions of the present invention will be described clearly and completely below in connection with the drawings, and obviously, the described embodiments are part of the embodiments of the present invention, but not all the embodiments. Based on the embodiments of the present invention, all other embodiments obtained by those having ordinary skill in the art without the exercise of inventive faculty are within the scope of the present invention.

The technical features involved in the different embodiments described throughout the full text of the present invention can be implemented in combination with each other.

Example 1 Production of Anti-CD25 Monoclonal Antibody 1.1 Immunization Scheme

Figure 1:
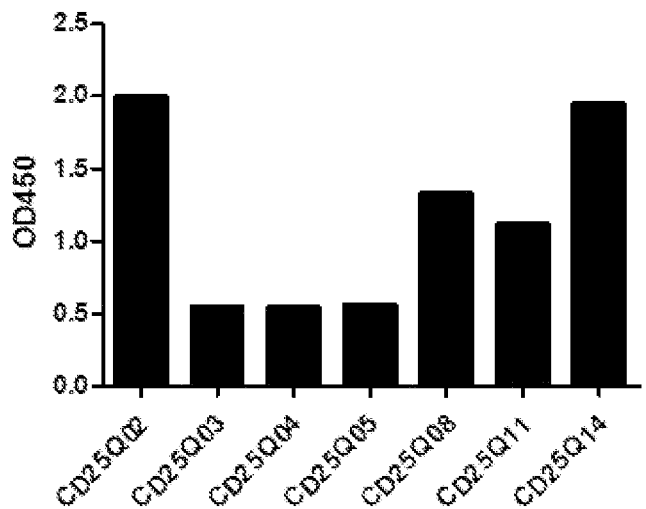
FIG. 1 shows the serum titers of BoAn-hMab1 mouse of an immunization scheme in Example 1 after seven immunizations (62500-fold dilution)

The CD25 (Sino Biological, catalog NO. 10165-H08H) is emulsified with Freund's adjuvant to immunize fully human antibody transgenic mouse BoAn-hMab1 of Boan bio (prepared according to the method described in Chinese Patent CN103571872B). The first immunization uses Freund's complete adjuvant (Sigma, catalog number: F5881-10ML), the second immunization to the sixth immunization use Freund's incomplete adjuvant (Sigma, catalog number: F5506-10ML), total of 14 mice were immunized at this time. 7 mice with higher serum titers were selected for booster immunization, and the mice were sacrificed 3 days later to remove the spleen for subsequent experiments. The serum titers (62500-fold dilution) of the mice are shown in FIG. 1.

1.2 Establishment of Phage Library

RNA is extracted from the spleen cells of the immunized mice in 1.1, and then reverse-transcribed into cDNA, the steps for establishing the phage library are performed referring to the method described in Carlos F. Barbas III, Phage display: A laboratory manual, the variable regions of the heavy and light chains are obtained from the cDNA by PCR method, and then scFv is obtained by overlapping extension PCR of the variable regions of the heavy chain and the light chain, scFv is ligated with plasmid pCOMB3× after digesting, and then the ligation product is electrotransfected into $E.\ coli$ TG1 competent cells, add the phage to infect TG1 after being incubated, and the supernatant of the culture concentrated is the phage library of the present invention.

1.3 Phage Library Screening (Two Methods)

(1) Plate screening: the plate is coated with CD25 protein (Sino Biological, 10165-H08H) at 1 μg/well, and left overnight at 4° C., the plate is sealed with 2% BSA for 1 h the next day, and added to a phage library ($2 \times 10^{12}$) to incubate for 2 h, and the phage specifically bound to CD25 is eluted with elution buffer (add 4.2 ml of concentrated hydrochloric acid (Comeo) to 500 ml of ultrapure water and adjust pH to 2.2 with glycine powder (Biotopped, BG0617-500)) or 15 μg/mL MA251 after being washed 4-10 times.

(2) Magnetic bead screening: CD25-Fc protein (Sino Biological, 10165-H02H) is biotinylated according to the general steps, and bound to Thermo's magnetic beads (Invitrogen Dynabeads M-280 Streptavidin, 00355871) and then incubated with the phage library, and the phage specifically bound to CD25 is eluted with elution buffer (pH 2.2) or 15 μg/mL MA251 after being washed 4-10 times.

The screened phage clones express scFv, and detect the binding of scFv and CD25, and detect the blocking of scFv on IL2/CD25 binding, and select scFv that binds well to CD25 and does not block CD25 for subsequent construction.

ELISA detection of binding of scFv and CD25: Preparation of CBS buffer: 1.59 g of $Na_2CO_3$ (Sinopharm, 10019260) and 2.93 g of $NaHCO_3$ are weighed, and the distilled water was added to 1 L to prepare CBS buffer. The CD25 (10165-H08H, Sino Biological) protein was diluted to 0.2 μg/mL with pH 9.6 CBS, coated with enzyme-labeled plate, 100 μL/well, and incubated overnight at 4° C.; 3% defatted milk powder was used for sealing at 37° C. for 1 h after washing the plate; 80 μL of PBST (PBS+0.05% Tween20) is added after washing the plate, and then 20 μL of scFv periplasm was added to incubate at 37° C. for 1 h. An anti-flag secondary antibody (Proteintech, catalog number: HRP-66008) was added after washing the plate to incubate at 37° C. for 1 h. 100 μL of TMB (Makewonder, catalog NO. 1001) substrate was added to each well for color development after washing the plate, 50 μL of 2M $H_2SO_4$ was added to each well to stop the color development after 10 mins, and OD450 was read with a microplate reader.

ELISA detection of blocking of scFv on CD25/IL2 binding: the CD25 (10165-H08H, Sino Biological) protein was diluted to 0.5 μg/mL with pH 9.6 CBS, and coated with enzyme-labeled plate, 100 μL/well, and incubated overnight at 4° C.; 3% defatted milk powder was used for sealing at 37° C. for 1 h after washing the plate. 50 μL of scFv periplasm was added to each well after washing the plate. Then, biotin-labeled IL2 protein (final concentration is 0.02 μg/mL) was added, 50 μL/well, and incubated at 37° C. for 1 h; STREP/HRP diluted with PBST was added after washing the plate, 100 μL/well, and incubated at 37° C. for 1 h. 100 μL of TMB is added to each well for color development after washing the plate, and 50 μL of 2M H2SO4 was added to each well to stop the color development after 10 mins, OD450 was read with a microplate reader.

Example 2 Molecular Construction and Production of Candidate Antibody

Magnetic bead screened clones CD25Q2-BA3\BA9\BA125, CD25Q8-BT942, CD25Q11-BA402\BA406\BA410\BA415\BA422\BA428 and CD25Q14-BA443\BA448\BA458 and plate screened clones CD25Q11-CA35\CA36\CT848 and CD25Q14-CA705\CA707\CA721 were sent to Invitrogen Biotechnology Ltd for sequencing. The amino acid sequences of the light chain variable region and the heavy chain variable region of each clone are set forth in Table 1.

TABLE 1 amino acid sequences of light chain variable region and heavy chain variable region of clones

| Clone ID | Light chain variable region sequence | Heavy chain variable region sequence |
| --- | --- | --- |
| BA3 | DIQMTQSPSTLSASVGDRVTITCRASQSLRSYLAWYQQKPGKAPKLLIYKASSLESGVPSRFSGSGSGTEFTLTISSLQPDDFATYYCQQYNSYTWTFGQGTKVEIK | QVQLQQWGAGLLKPSETLSLTCAVYGGSFSGYYWSWIRQPPGKGLEWIGEIDHSGSTIYNPSLKSRVTISLDTSKNQFSLNLTSVTAADTAVYYCARGEAFDIWGQGTMVTVSS |
| BA9 | DIVMTQSPSTLSASVGDRVTITCRASQSLRSYLAWYQQKPGKAPKLLIYKASSLESGVPSRFSGSGSGTEFTLTISSLQPDDFATYYCQQYNSYSWTFGQGTKVEIK (SEQ ID NO: 1) CDR region L-CDR1: QSLRSY (SEQ ID NO: 5) L-CDR2: KAS (SEQ ID NO: 6) L-CDR3: QQYNSYSWT (SEQ ID NO: 7) | QVQLQQWGAGLLKPSETLSLTCAVYGGSFSGYYWSWIRQPPGKGLEWIGEIDHSGSTIYNPSLKSRVTISLDTSKNQFSLKLSSVTAADTALYYCARGEAFDIWGQGTMVTVSS (SEQ ID NO: 2) CDR region H-CDR1: GGSFSGYY (SEQ ID NO: 8) H-CDR2: IDHSGST (SEQ ID NO: 9) H-CDR3: ARGEAFDI (SEQ ID NO: 10) |
| BA125 | DIQMTQSPSTLSASVGDRVTITCRASQIISGYLAWYQQKPGKAPKLLIYKASSLESGVPSRFSGSGSGAEFTLTISSLQPDDFATYYCQQYNSYTWTFGQGTKVEIK | EVQLVQSGAEVKKPGESLKISCKGSGYSFANYWIVWVRQMPGKGLEWMGIIYPDDSETRYSPSFQGQVTFSADKSISTAYLQWSSLKASDTAMYYCTRGPYYSDYWGQGTLVTVSS |
| CA35 | DIQMTQSPSTLSASVGDRVTITCRASQSISSWLAWYQQKPGKAPKLLIYKASSLESGVPSRFSGSGSGTEFTLTISSLQPDDFATYYCQQYNSYTWTFGQGTKVEIK | QVQLVQSGAEVKKPGESLKISCKGSGYSFTNYWIGWVRQMPGKGLEWMGIIYPGDSVTRYSPSFQGQVTISADKSINTAYLQWSSLRASDTAMYYCARGPYYFEYWGQGTLVTVSS |
| CA36 | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPYTFGQGTKVEIK | QVQLVQSGAEVKQPGSSVKVSCKTSGGTFGSSAINWVRQAPGQGLEWMGRIIPIFGVSNFAQKFQGRVTITADKSTNTAYMELSSLRSEDTAVYYCARDGSGYDSNYWYFDLWGRGTLVTVSS |
| BA402 | DIVMTQSPSTLSASVGDRVTLTCRASQSISSYLAWYQQKPGKAPKLLIYKASTLESGVPSRFSGSGSGTEFTLTISSLQPDDFATYYCQHYNSYSVTFGGGTKVEIK | QVQLVQSGAEVKKPGESLKISCKGSGYSFSNYWIAWVRQMPGKGLEWMGIIYPGDSATRYSPSFQGQVTISADKSINTAYLQWSSLRASDTAMYYCARGPYYFEYWGQGTLVTVSS |
| BA410 | DIQMTQSPSTLSASVGDRVTITCRASQSISSWLAWYQQKPGKAPKLLIYKASSLESGVPSRFSGSGSGTEFTLTISSLQPDDFATYYCQQYNSYSWTFGQGTKVEIK | QVQLQQWGAGLLKPSETLSLTCAVYGGSFSGHYWSWIRQSPGKGLEWIGEIDHSGNAIYNPSLKSRVTISIDTSKNQFSLKLSSVTAADTAVYYCARGEAFDLWGQGTMVTVSS |
| BA415 | DIQMTQSPSTLSASVGDRVTITCRASQSISTWLAWYQQKPGKAPKLLIYKASSLESGVPSRFSGSGSGTEFTLTISSLQPDDFAAYYCQQYSSYSWTFGQGTKVEIK | QVQLVQSGTEVKKPGESLKISCEGVGYSFTTYWIGWVRQMPGKGLEWMGIIYPGDSITRYSPSFQGQVTISADKSINTAYLQWSSLMASDTAMYCVRGPHWGDYWGQGTLVTVSS |
| BA422 | DIQMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPYTFGQGTKVEIK | QVQLVQSGAEVKKPGSSVKVSCKASGGTFSSSAISWVRQAPGQGLDWMGRIIPLLNIADYAQKFQGRVTFTADKSTNTAYMELSSLRSEDTAVYYCARDGSGYDSNYWYFDLWGRGTLVTVSS |
| BA428 | DIVMTQSPSTLSASVGDRVTITCRASQSISSWLAWYQQKPGKAPKLLIYKASSLESGVPSRFSGSGSGTEFTLTISSLQPDDFATYYCQQYNSYSLTFGGGTKVEIK | QVQLVQSGAEVKKPGESLKISCKGSGYSFTNYWIVWVRQMPGKGLEWMGIISPGDSTTRYSPSFQGQVTFSADKSISTAYLQWSSLKASDTAMYYCAIGPYYLEYWGQGTLVTVSS |

TABLE 1-continued amino acid sequences of light chain variable region and heavy chain variable region of clones

| Clone ID | Light chain variable region sequence | Heavy chain variable region sequence |
|---|---|---|
| BA443 | DIQMTQSPSTLSASVGDRVTITCRASQ SVSGYLAWYQQKPGKAPKLLIYKTSS LESGVPSRFSGSGSGTDFTLTISSLQAE DVAVYYCQQYYSTPWTFGQGTKVEIK | EVQLVQSGAEVKKPGESLKISCKGS GYSFSNYWIGWVRQMPGKGLEWM GIISPGDSTTKYSPSFQGQVTFSADK STSTAYLQWSSLQASDTAMYYCVR GPYYLDYWGQGTLVTVSS |
| BA448 | DIQMTQSPSTLSASVGDRVTITCRASQ SISSWLAWYQQKPGKAPKLLIYKASS LESGVPSRFSGSGSGTEFTLTISSLQPD DFATYYCQQYDRFSWTFGQGTKVEIK | EVQLVQSGAEVKKPGESLKISCKGS GYNFANYWIVWVRQMPGKGLEW MGITYPDDSETRYSPSFQGQVTFSAD KSISTAYLQWSSLKASDTAMYYCTR GPYYSDYVVGQGTLVTVSS |
| BA458 | DIQMTQSPSTLSASVGDRVTITCRASQ SISSWLAWYQQKPGKAPKLLIYKASS LESGVPSRFSGSGSGTEFTLTISSLQPD DFATYYCQQYNSYLLTFGGGTKLEIK | EVQLVQSGAEVKKPGESLKISCKGS GYSFSNYWIGWVRQMPGKGLEWM GIISPGDSTTKYSPSFQGQVTFSADK STSTAYLQWSSLQASDTAMYYCVR GPYYLDYWGQGTLVTVSS |
| CA705 | DIQMTQSPSTLSASVGDRVSITCRASQ SIGSWLAWYQQKPGKAPKLLIFEASN LESGVPSRFSGSGSGTEFTLTISNLQPD DFATYYCQQYNSYSLTFGGGTKVEIK | EVQLVQSGAEVKKPGESLKISCKGS GYSFANYWIVWVRQMPGKGLEWM GIIYPDDSETRYSPSFQGQVTFSADK SISTAYLQWSSLKASDTAMYYCTRG PYYSDYWGQGTLVTVSS |
| CA707 | DIQMTQSPSTLSASVGDRVTITCRASQ SVSSWLAWYQQKPGKAPKLLIYKASS LESGVPSRFSGSGSGTEFTLTISSLQPD DFATYYCQQYSSYSWTFGQGTKVEIK | EVQLVQSGAEVKKPGESLKISCKGS GYSFSNYWIGWVRQMPGKGLEWM GIISPGDSTTKYSPSFQGQVTFSADK STSTAYLQWSSLQASDTAMYYCVR GPYYLDYWGQGTLVTVSS |
| CA721 | DIQMTQSPSTLSASVGDRVTITCRASQ SVSSWLAWYQQKPGKAPKLLIYKASS LESGVPSRFSGSGSGTEFTLTISSLQPD DFATYYCQQYSSYSWTFGQGTKVEIK | QVQLVQSGAEVKKPGESLKISCKGS GYSFANYWIVWVRQMPGKGLEWM GIIYPDDSETRYSPSFQGQVTFSADK SISTAYLQWSSLKASDTAMYYCTRG PYYSDYWGQGTLVTVSS |
| CT848 | DIVMTQSPSTLSASVGDRVTITCRASQ SVSSWLAWYQQKPGKAPKLLIYKASS LESGVPSRFSGSGSGTEFTLTISSLQPD DFATYYCQQYSSYSWTFGQGTKVEIK | QVQLQQWGAGLLKPSETLSLTCAV YGGSFSGSYWSWIRQSPRKGLEWI GEIDHSGSTIANPSLKSRITISLDTSK NQFFLQLRSMTAADTAVYYCARGE AFDIWGQGTMVTVSS |
| BT942 | DIQMTQSPDSLAVSLGERATINCKSSQ SVLYSSNNKNYLAWYQQKPGQPPKL LIYWASTRESGVPDRFSGSGSGTDFTL TISSLQAEDVAVYYCQQYYSTPYTFG QGTKVEIK (SEQ ID NO: 3) CDR region L-CDR1: QSVLYSSNNKNY (SEQ ID NO: 11) L-CDR2: WAS (SEQ ID NO: 12) L-CDR3: QQYYSTPYT (SEQ ID NO: 13) | QVQLVQSGAEVKKPGSSVKVSCKA SGGTFSSDAINWVRQAPGQGLEWM GRIIPIFGVADYAQKFQGRVTLTADK STSTAYMDLSSLRSEDTAVFYCARE RGDYSNFWYFDLWGRGTLVTVSS (SEQ ID NO: 4) CDR region H-CDR1: GGTFSSDA (SEQ ID NO: 14) H-CDR2: IIPIFGVA (SEQ ID NO: 15) H-CDR3: ARERGDYSNFWYFDL (SEQ ID NO: 16) |
| BA406 | DIVMTQSPSTLSASVGDRVTITCRASQ SISSFLAWYQQKPGRAPELLIYKASTL ESRVPSRFSGSGSGTEFTLTISSLQPED FATYYCQQYKSFSWTVGQGTKVEIK | EVQLVQSGAEVKKPGESLKISCKGS GYSFTNYWIAWVRQMPGKGLEWM GIIYPGDSVTRYSPSFQGQVTISADK SINTAYLQWSSLRASDTAMYYCAR GPYYFEYWGQGTLVTVSS |

The nucleotide sequence fragment encoding VH was finally inserted into the vector pCDNA3.4 (Life Technology) with the nucleotide sequence encoding the heavy chain constant region amino acid sequence SEQ ID NO: 17 of the antibody, the nucleotide sequence fragment encoding VL was inserted into the vector pCDNA3.4 (Life Technology) with the nucleotide sequence encoding the light chain constant region amino acid sequence (SEQ ID NO: 20) of the antibody, through variable region gene amplification (2*Phanta Max Master Mix, manufacturer: Vazyme, Item No.: P515-AA, Lot No.: TE211 GB), signal peptide and variable region overlap extension, homologous recombination (ClonExpress II One Step Cloning Kit, manufacturer: Vazyme, Item No.: C112-01, Lot No.: TE211 L8) and the like, performed by conventional molecular biology techniques. The linked vector is transfected into HEK293 cells and incubated in 37° C.\8% CO2\125 rpm shaker, and after transiently expressing 6-7 days, the supernatant was purified by Protein A affinity chromatography to obtain anti-CD25 antibody, and the antibody concentration was determined by UV280 binding extinction coefficient.

Production of control antibody: MA251 antibody is an anti-human CD25 antibody that does not block the binding of IL2 and CD25 in the prior art, has a high affinity for human CD25, and has a good performance of not blocking the binding of IL2 and CD25. The MA251 antibody is a classic antibody studying the binding of IL2 and CD25. The nucleotide sequence encoding the variable region of the MA251 antibody is synthesized by the complete gene and then inserted into the vector pCDNA3.4 and expressed by HEK293 cells, and the produced antibody is named CD25-MA251-IgG1 (the sequence of the heavy chain variable region is SEQ ID NO: 18, the sequence of the light chain variable region is SEQ ID NO: 19, the sequence of the light chain constant region is SEQ ID NO: 20, and the sequence of the heavy chain constant region is SEQ ID NO: 17).

Example 3 Characterization of Candidate Antibody 3.1 ELISA Detection of Activity of Binding of Candidate Antibody and CD25 Protein The CD25 protein (10165-H08H, Sino Biological) was diluted to different concentrations (0.08 μg/mL, 0.02 μg/mL, 0.005 μg/mL, 0.00125 μg/mL, 0.0003125 μg/mL, 0.000078125 μg/mL) with CBS, was coated with enzyme-labeled plate, 100 μL/well, and incubated overnight at 4° C.; 3% defatted milk powder was used for sealing at 37° C. for 1 h after washing the plate; 100 μL of candidate antibody that was diluted to 1 μL/mL with PBST (PBS+0.05% Tween20) was added to each well, and incubated at 37° C. for 1 h; then the goat anti-human IgG/HRP (KPL, catalog number: 5450-0009) was added and incubated at 37° C. for 1 h, and after color developing for 10 min, OD450 was read on a microplate reader to obtain $EC_{50}$ by calculating. The results are shown in FIG. 2A to FIG. 2E and Table 2 to Table 6.

As shown in Table 2, a $EC_{50}$ value of the binding of the candidate antibody CD25Q2-BA9-IgG1 and antigen CD25 is 3.328, which is significantly lower than the $EC_{50}$ value of the control group CD25-MA251-IgG1 that is 10.63, which indicates that the antigen binding capacity of the candidate antibody is significantly better than that of the control group CD25-MA251-IgG1.

As shown in Table 6, a $EC_{50}$ value of the binding of the candidate antibody CD25Q2-BA9-IgG1 and antigen CD25 is 2.26, which is significantly lower than the $EC_{50}$ value of the control group CD25-MA251-IgG1 that is 24.5, which indicates that the antigen binding capacity of the candidate antibody is significantly better than that of the control group CD25-MA251-IgG1.

It is predicted that the candidate antibodies CD25Q2-BA9-IgG1 and CD25Q8-BT942-IgG1 have a stronger targeting and binding effect on the Treg cells expressing CD25, have better killing effect, reduce inhibition of the Treg cells on the Teff cells, and have better pharmaceutical effects as compared with the control group CD25-MA251-IgG1.

TABLE 2

Figure 2A:
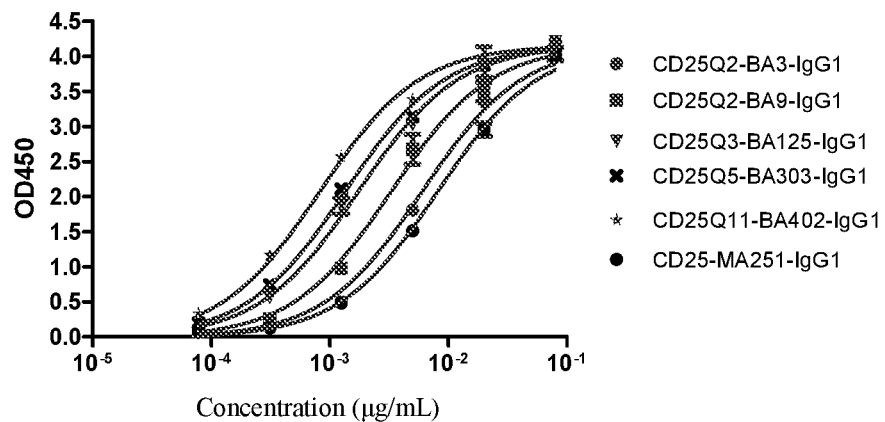
FIG. 2A to FIG. 2E show the sensitivity of the binding of CD25 antibody and CD25 by ELISA detection in Example 3.

Data of ELISA detection of activity of binding of candidate antibody and CD25 protein (corresponding to FIG. 2A)

| Antibody name | $EC_{50}$ (ng/mL) | Antibody name | $EC_{50}$ (ng/mL) |
|---|---|---|---|
| CD25Q2-BA3-IgG1 | 7.375 | CD25Q5-BA303-IgG1 | 1.202 |
| CD25Q2-BA9-IgG1 | 3.328 | CD25Q11-BA402-IgG1 | 0.6743 |
| CD25Q3-BA125-IgG1 | 1.608 | CD25-MA251-IgG1 | 10.63 |

TABLE 3

Figure 2B:
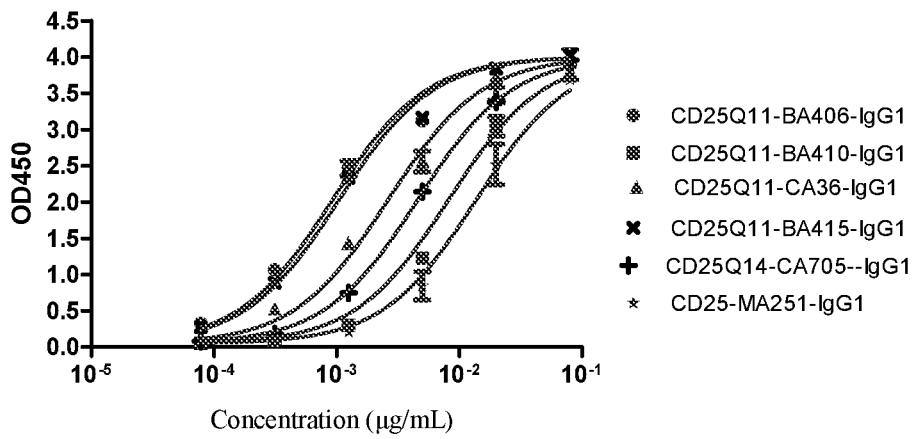

Data of ELISA detection of activity of binding of candidate antibody and CD25 protein (corresponding to FIG. 2B)

| Antibody name | $EC_{50}$ (ng/mL) | Antibody name | $EC_{50}$ (ng/mL) |
|---|---|---|---|
| CD25Q11-BA406-IgG1 | 0.6515 | CD25Q11-BA415-IgG1 | 0.9405 |
| CD25Q11-BA410-IgG1 | 16.82 | CD25Q14-CA705-IgG1 | 4.773 |
| CD25Q11-CA36-IgG1 | 2.41 | CD25-MA251-IgG1 | 14.06 |

TABLE 4

Figure 2C:
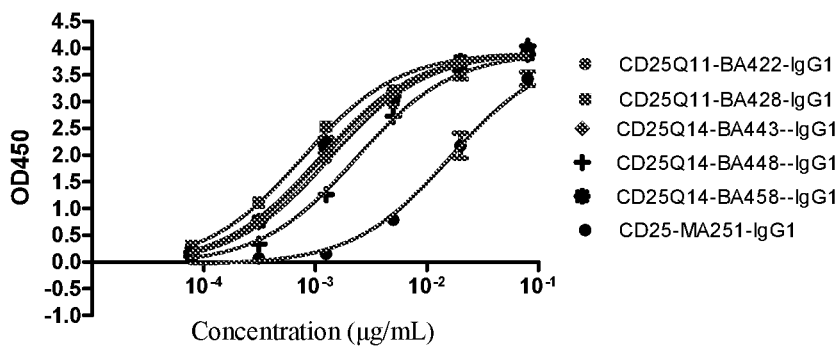

Data of ELISA detection of activity of binding of candidate antibody and CD25 protein (corresponding to FIG. 2C)

| Antibody name | $EC_{50}$ (ng/mL) | Antibody name | $EC_{50}$ (ng/mL) |
|---|---|---|---|
| CD25Q11-BA422-IgG1 | 1.304 | CD25Q14-BA448-IgG1 | 2.684 |
| CD25Q11-BA428-IgG1 | 0.5974 | CD25Q14-BA458-IgG1 | 1.003 |
| CD25Q14-BA443-IgG1 | 1.06 | CD25-MA251-IgG1 | 16.98 |

TABLE 5

Figure 2D:
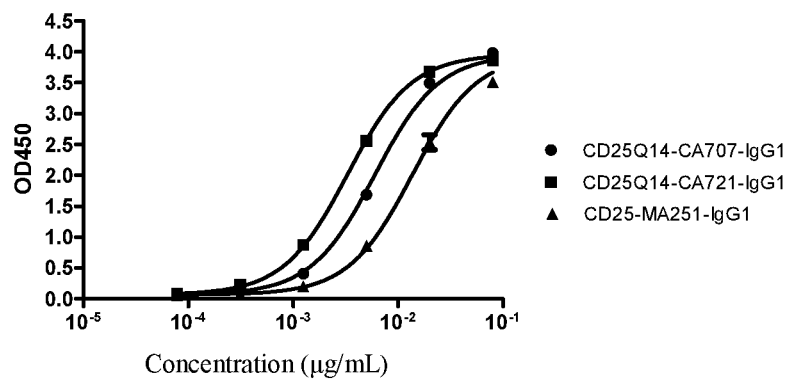

Data of ELISA detection of activity of binding of candidate antibody and CD25 protein (corresponding to FIG. 2D)

| Antibody name | $EC_{50}$ (ng/mL) | Antibody name | $EC_{50}$ (ng/mL) |
|---|---|---|---|
| CD25Q14-CA707-IgG1 | 6.415 | CD25-MA251-IgG1 | 12.09 |
| CD25Q14-CA721-IgG1 | 3.252 | / | / |

TABLE 6

Figure 2E:
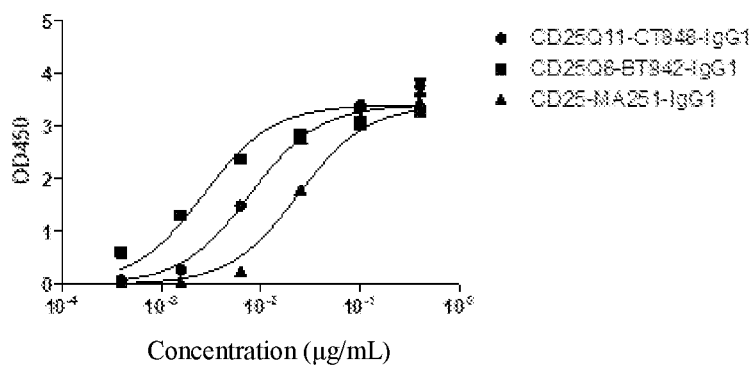

Data of ELISA detection of activity of binding of candidate antibody and CD25 protein (corresponding to FIG. 2E)

| Antibody name | $EC_{50}$ (ng/mL) | Antibody name | $EC_{50}$ (ng/mL) |
|---|---|---|---|
| CD25Q11-CT848-IgG1 | 9.162 | CD25-MA251-IgG1 | 24.5 |
| CD25Q8-BT942-IgG1 | 2.26 | / | / |

3.2 Detection of Simulated Killing Activity of Candidate Antibody

FBS (Gibco, catalog number: 10091-148) and RPMI-1640 (Gibco, catalog number: 11875-093) were mixed according to 1:99 to prepare 1% FBS RPMI-1640, SU-DHL-1 target cells were collected, and was diluted to $1.2 \times 10^6$ cells/mL by using 1% FBS RPMI-1640, appropriate candidate antibody was taken and diluted to 25 μg/mL by using 1% FBS RPMI-1640, this concentration was used as an initial concentration; diluted 4 times in gradient in sequence to a total of 8 points for future use; effector cells Jurkat (G7011, Promega) were collected, and diluted to $2.4 \times 10^6$ cells/mL by using 1% FBS RPMI-1640, target cells were added in the white 96-well plate with 25 μL/well; the antibody diluted in gradient was added in the wells covered with target cells, with 25 μL/well; effector cells Jurkat were added with 25 μL/well, and the 96-well plate was placed into the cell incubator to culture 5 h; and the 96-well plate was removed and placed at room temperature to enable the temperature thereof to equilibrate to room temperature; Bio-Gl chromogenic solution (G7940, Promega) was added with 75 μL/well, reacting for 15 mins, Luminescense was read from a Tecan microplate reader to obtain a value. The results are shown in FIG. 3A to FIG. 3B and Table 7 to Table 8.

TABLE 7

Figure 3A:
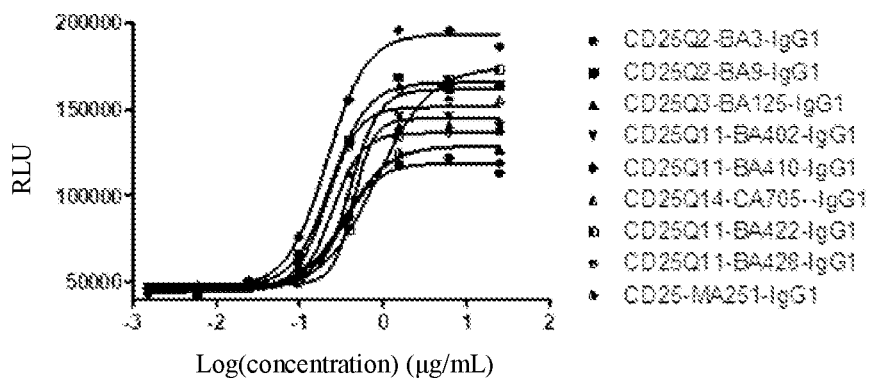
FIG. 3A to FIG. 3B show the detection results of the simulated killing activity of the candidate antibodies in Example 3.
Figure 3B:
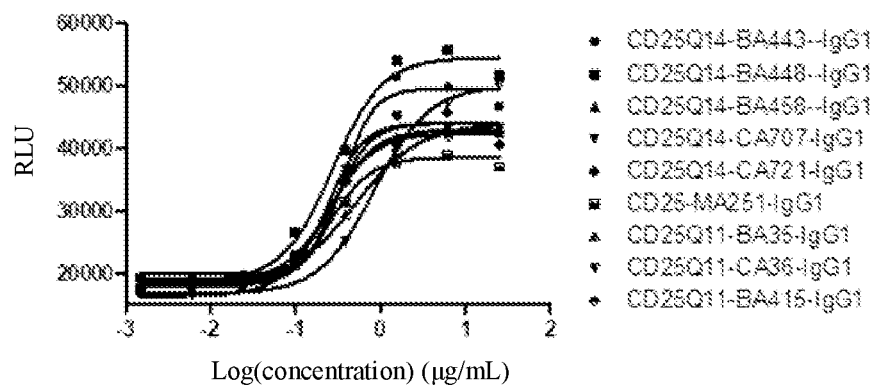

Result of simulated killing activity detection of candidate antibody (corresponding to FIG. 3A)

| Antibody name | $EC_{50}$ (Mg/mL) | Antibody name | $EC_{50}$ (Mg/mL) |
|---|---|---|---|
| CD25Q2-BA3-IgG1 | 0.3310 | CD25Q14-CA705-IgG1 | 0.4094 |
| CD25Q2-BA9-IgG1 | 0.2356 | CD25Q11-BA422-IgG1 | 0.8362 |
| CD25Q3-BA125-IgG1 | 0.2512 | CD25Q11-BA428-IgG1 | 0.2170 |
| CD25Q11-BA402-IgG1 | 0.4429 | CD25-MA251-IgG1 | 0.3606 |
| CD25Q11-BA410-IgG1 | 0.2149 | / | / |

TABLE 8

Result of simulated killing activity test of candidate antibody (corresponding to FIG. 3B)

| Antibody name | $EC_{50}$ (Mg/mL) | Antibody name | $EC_{50}$ (Mg/mL) |
|---|---|---|---|
| CD25Q14-BA443-IgG1 | 0.3604 | CD25Q11-BA35-IgG1 | 0.5040 |
| CD25Q14-BA448-IgG1 | 0.2756 | CD25Q11-CA36-IgG1 | 0.8569 |
| CD25Q14-BA458-IgG1 | 0.2656 | CD25Q11-BA415-IgG1 | 0.2332 |
| CD25Q14-CA707-IgG1 | 0.2476 | CD25-MA251-IgG1 | 0.2546 |
| CD25Q14-CA721-IgG1 | 0.2879 | / | / |

As shown in Table 7, the $EC_{50}$ value of simulated killing activity detection of the candidate antibody CD25Q2-BA9-IgG1 is 0.2356, which is lower than the $EC_{50}$ value of the control group CD25-MA251-IgG1 that is 0.3606, which indicates that the killing ability of the candidate antibody to SU-DHL-1 is better than that of the control group CD25-MA251-IgG1.

The above results indicate that the candidate antibody CD25Q2-BA9-IgG1 has a good killing effect on cells expressing CD25, which predicts that the candidate antibody can reduce the Treg cells expressing CD25 and their inhibition on Teff cells, thereby having better pharmaceutical effects.

3.3 BiaCore Detection of Affinity of Antibody

Antibody binding kinetics uses BIAcore8K instrument based on surface plasmon resonance (SRP) technology to measure. Anti-human IgG antibody amino was coupled to a CMS biosensor chip by the GE anti Human IgG Fc amino coupling kit (GE, cat #BR-1008-39) to obtain approximately 1000 response units (RU). For kinetic measurements, the CD25 protein (Sino Biological, 10165-H08H) was diluted 2-fold continuously with HBS-EP+1×(GE, BR-1008-26) buffer, starting at 50 nM, being diluted 2-fold for 4 concentration gradients and setting 0 concentration. The antibody to be detected: 2 μg/ml, sample injection time 70 s, flow rate 5 μL/min, stable for 5 s; CD25 protein: binding for 60 s, flow rate 30 μL/min, dissociation for 450 s; regeneration: regeneration was performed for 30 s with 3M $MgCl_2$ buffer, Startup 3 times. The association constant (ka) and dissociation constant (kd) were calculated using a simple one-to-one Languir binding model (BIAcore Evaluation Software version 3.2), and the equilibrium dissociation constant (KD) was calculated by the ratio kd/ka. The affinity data of each antibody is shown in Table 9.

TABLE 9

Data of BiAcore detection of candidate antibody binding kinetics

| Antibody name | ka(1/Ms) | kd(1/s) | KD(M) |
|---|---|---|---|
| CD25Q2-BA3-IgG1 | 4.56E+05 | 1.36E+−03 | 2.98E+−09 |
| CD25Q2-BA9-IgG1 | 6.96E+05 | 5.86E+−04 | 8.43E+−10 |
| CD25Q11-CA36-IgG1 | 6.02E++04 | 9.66E+−05 | 1.61E+−09 |
| CD25Q3-BA125-IgG1 | 6.99E+05 | 3.01E+−04 | 4.31E+−10 |
| CD25Q11-BA402-IgG1 | 3.50E+05 | 2.12E+−04 | 6.07E+−10 |
| CD25Q11-BA410-IgG1 | 1.40E++06 | 6.74E+−03 | 4.81E+−09 |
| CD25Q11-BA415-IgG1 | 3.23E+05 | 1.99E+−04 | 6.14E+−10 |
| CD25Q11-BA428-IgG1 | 5.55E+05 | 2.10E+−04 | 3.79E+−10 |
| CD25Q14-BA443-IgG1 | 1.36E+05 | 2.01E+−04 | 1.48E+−09 |
| CD25Q14-BA448-IgG1 | 5.87E+05 | 5.31E+−04 | 9.04E+−10 |
| CD25Q14-BA458-IgG1 | 3.62E+05 | 2.16E+−04 | 5.96E+−10 |
| CD25Q14-CA705-IgG1 | 3.81E+05 | 7.52E+−04 | 1.97E+−09 |
| CD25Q14-CA707-IgG1 | 3.31E+05 | 9.44E+−04 | 2.85E+−09 |
| CD25Q14-CA721-IgG1 | 6.80E+05 | 3.65E+−04 | 5.36E+−10 |
| CD25Q11-CT848-IgG1 | 7.05E+05 | 2.18E+−03 | 3.09E+−09 |
| CD25Q8-BT942-IgG1 | 8.96E++04 | 3.39E+−04 | 3.79E+−09 |
| CD25-MA251-IgG1 | 1.76E+05 | 9.12E+−04 | 5.19E+−09 |

As shown in Table 9, the equilibrium dissociation constant KD value of the candidate antibody CD25Q2-BA9-IgG1 is 8.43E-10, which is lower than the KD value of the control group CD25-MA251-IgG1 that is 5.19E-09, which indicates that the affinity of CD25 protein of the candidate antibody CD25Q2-BA9-IgG1 is better than that of the control group CD25-MA251-IgG1.

As shown in Table 9, the equilibrium dissociation constant KD value of the candidate antibody CD25Q8-BT942-IgG1 is 3.79E-09, which is lower than the KD value of the control group CD25-MA251-IgG1 that is 5.19E-09, which indicates that the affinity of CD25 protein of the candidate antibody CD25Q8-BT942-IgG1 is better than that of the control group CD25-MA251-IgG1.

The above results predict that the candidate antibodies CD25Q2-BA9-IgG1 and CD25Q8-BT942-IgG1 have a stronger targeting and binding effect on the Treg cells expressing CD25, have better killing effect, reduce inhibition of the Treg cells on the Teff cells, and have better pharmaceutical effects as compared with the control group CD25-MA251-IgG1.

3.4 Cell Blocking Activity of Candidate Antibody

Figure 4:
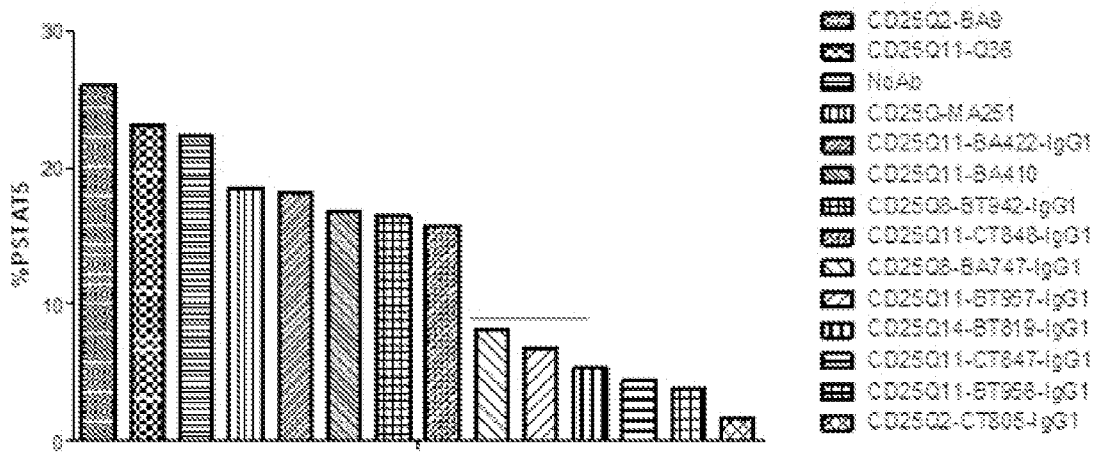
FIG. 4 shows the detection results of the cell blocking activity of the candidate antibodies in Example 3.

The frozen PBMC (peripheral blood mononuclear cells, manufacturer: ALLCELLS, item no.: PB003F-C) were recovered and then co-cultured with 10 μg/mL of CD25 antibody on the 96-U bottom plate for 30 mins, no antibody was added to the control group, the control group was labeled as NoAb, and then IL2 (0.1 U/mL, 1 U/mL, 10 U/mL) was added to incubate for 10 mins (working medium: 1640+10% FBS, containing 2 mM L-glutamine and 10000 U/mL Pen-Strep), to prepare cell suspension: after the last washing, the supernatant was discarded and the sample was vortexed on pulse to completely dissociate the pellet; 200 μL Foxp3 fixation/permeabilization working solution was added to each well. It was incubated at 2-8° C. or room temperature in the dark for 30-60 minutes; the sample was centrifuged at 400-600 g for 5 minutes at room temperature, and the supernatant was discarded; 200 μL of 1× membrane breaking solution was added to each well, the sample was centrifuged at 400-600 g for 5 minutes at room temperature, the supernatant was discarded, and is washed twice; (BD Phosflow™ Perm Buffer III is preliminarily put at −20° C. to pre-cool) washed with PBS once, centrifuged and the supernatant being discarded; ice-cold Phosflow™ Perm Buffer III was added slowly while being vortexed, and incubated on ice for 30 minutes; the cells were washed twice with PBS, centrifuged at 250 g for 10 minutes to discard the supernatant; the cells were resuspend in PBS to $10^7$ cells/mL, contained separately in 100 μL/well, the antibody staining fluorescently labeled was continued and the flow cytometry was performed; living cells were distinguished, and the CD3 positive T cells were further distinguished. The higher the percentage of phosphorylated signal transducers and transcription activator 5 (PSTAT5), the lower the blocking rate. The results are shown in FIG. 4 and Table 10.

As shown in Table 10, the % PSTAT5 value of the candidate antibody CD25Q2-BA9-IgG1 is 26.09, which is significantly higher than the % PSTAT5 value of the control group CD25-MA251-IgG1 that is 18.52, which indicates that the candidate antibody is significantly better than the control group CD25-MA251-IgG1 in not blocking the binding of IL2 and PBMC. It indicates that the candidate antibody CD25Q2-BA9-IgG1 can inhibit the activation of PBMC less than the control group CD25-MA251-IgG1, which predicts that the candidate antibody CD25Q2-BA9-IgG1 can better achieve the PBMC immune effect and have better pharmaceutical effect/anti-tumor effect.

As shown in Table 10, the % PSTAT5 value of the candidate antibody CD25Q8-BT942-IgG1 is 16.46, and the % PSTAT5 value of CD25-MA251-IgG1 is 18.52, which indicates that the candidate antibody basically equivalent to the control group CD25-MA251-IgG1 in not blocking the binding of IL2 and PBMC. It predicts that the candidate antibody CD25Q8-BT942-IgG1 can well achieve the PBMC immune effect and have good pharmaceutical effect/anti-tumor effect.

TABLE 10

Data of cell blocking activity of candidate antibody (corresponding to FIG. 4)

| Antibody name | % PSTAT5 | Antibody name | % PSTAT5 |
|---|---|---|---|
| CD25Q2-BA9 | 26.09 | CD25Q11-CT848-IgG1 | 15.76 |
| CD25Q11-Q36 | 23.08 | CD25Q8-BA747-IgG1 | 8.1 |
| NoAb | 22.38 | CD25Q11-BT957-IgG1 | 6.72 |
| CD25Q-MA251 | 18.52 | CD25Q14-BT819-IgG1 | 5.3 |
| CD25Q11-BA422-IgG1 | 18.09 | CD25Q11-CT847-IgG1 | 4.41 |
| CD25Q11-BA410 | 16.84 | CD25Q11-BT956-IgG1 | 3.78 |
| CD25Q8-BT942-IgG1 | 16.46 | CD25Q2-CT805-IgG1 | 1.68 |

Example 4 In Vivo Activity of Candidate Antibody 4.1 PD Activity of CD25Q2-BA9-IgG1 in Healthy Rhesus Monkey CD25Q2-BA9-IgG1 antibody was administered intravenously to 3 rhesus monkeys at a dose of 10 mg/kg, flow cytometer (Cytomics™ FC500) was used to detect the content of the Treg cells (CD3+CD4+CD25+FoxP3+) at different time points before and after the administration according to flow cytometry, and the detection time points were: (±1 minute) before and after the administration, 0.5 hours (±1 minute), 3 hours (±2 minutes), 6 hours (±5 minutes), 24 hours (±10 minutes), 48 hours (±20 minutes, 2 days), 96 hours (±30 minutes, 4 days), 168 hours (±1 hour, 7 days), 336 hours (±1 hour, 14 days) after the administration, the experimental results are shown in FIG. 5.

Figure 5:
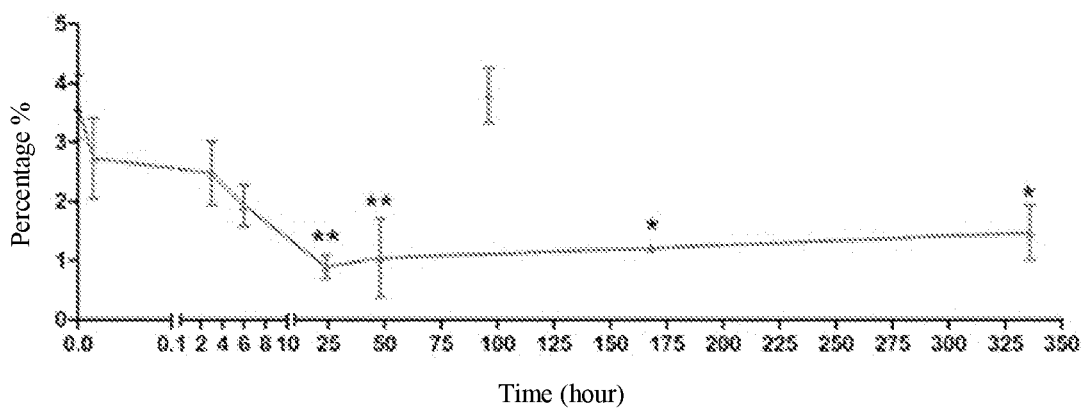
FIG. 5 shows the effect of CD25Q2-BA9-IgG1 on reducing the content of Treg cells of rhesus monkey in Example 4.

As can be seen from FIG. 5, after administration of CD25Q2-BA9-IgG1, it can significantly reduce the content of Treg cells in rhesus monkeys and can effectively regulate the immune microenvironment.

4.2 PK Activity of Candidate Antibody in Cynomolgus Monkey

Figure 6:
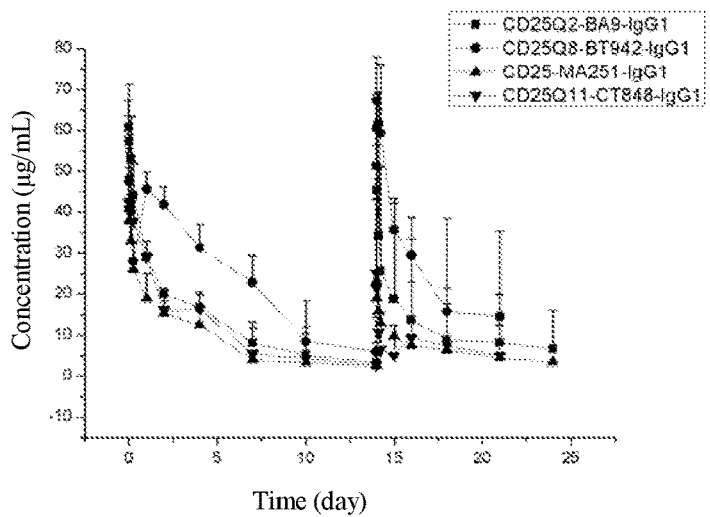
FIG. 6 shows the drug metabolism of the candidate antibody in cynomolgus monkey in Example 4.

There are two cynomolgus monkeys in each group, they were intravenously injected with different CD25 antibodies, and whole blood samples were taken out intravenously at (0 h) before the administration and 1 min, 30 min, 3 h, 6 h, 1 d, 2 d, 4 d, 7 d, 10 d, and 14 d after the administration, put in a blood sample collection tube, and coagulated naturally in the ice box, the blood sample was put in the centrifuge within 8 h after being taken out, centrifuged at 1000-3000 g for 10 mins, the serum was separated and put in the sample storage tube, and the cynomolgus monkeys were intravenously injected with different CD25 antibodies again on the 14th day, the whole blood samples were taken out intravenously at (0 h) before the administration and 1 min (14 d+1 m), 30 min (14 d+30 m), 3 h (14 d+3 h), 6 h (14 d+6 h), 1 d (15 d), 2 d (16 d), 4 d (18 d) and 7 d (21 d) after the administration, put in a blood sample collection tube, and coagulated naturally in the ice box, the blood sample were put in the centrifuge within 8 h after being taken out, centrifuged at 1000-3000 g for 10 mins, the serum was separated and put in the sample storage tube, the metabolism of antibodies in the cynomolgus monkeys was detected by ELISA, and the results are shown in FIG. 6 and Table 11.

The results indicate: CD25Q2-BA9-IgG1 and CD25Q8-BT942-IgG1 have a higher bioavailability than that of the control antibody CD25-MA251-IgG1, and have good pharmacokinetic performance.

TABLE 11

Metabolism of candidate antibody in cynomolgus monkey

| | Drug | $C_{max}$(μg/mL) | $C_0$(μg/mL) | $T_{1/2}$(hr) | $AUC_{0-t}$(hr*μg/mL) |
|---|---|---|---|---|---|
| First dose 2.5 mg/kg | CD25Q2-BA9-IgG1 | 61.61 | 60.945 | 118.695 | 4119.085 |
| | CD25-MA251-IgG1 | 40.975 | 41.09 | 268.74 | 2614.365 |
| | CD25Q11-CT848-IgG1 | 44.845 | 42.72 | 125.28 | 3316.56 |
| | CD25Q8-BT942-IgG1 | 72.72 | 70.675 | 167.52 | 7818.84 |
| Second dose 2.5 mg/kg | CD25Q2-BA9-IgG1 | 51.295 | 51.52 | 176.975 | 2703.66 |
| | CD25-MA251-IgG1 | 23.19 | 23.39 | 83.465 | 1529.25 |
| | CD25Q11-CT848-IgG1 | 26.63 | 21.49 | 68.52 | 1213.08 |
| | CD25Q8-BT942-IgG1 | 69.93 | 67.98 | 223.92 | 3916.56 |

Example 5 Efficacy of Candidate Antibody In Vivo Tumor Model 5.1 Efficacy Test of Candidate Antibody in B-hIL2Rα Humanized Mouse MC38 Colon Cancer Animal Model B-hIL2Rα humanized mice (Biocytogen) were divided into 5 groups according to body weight, wherein 10 mice was in the G1 negative control group and 8 mice were in each of the G2-G4 treatment groups. Individual administration was performed from the day of grouping (10 mg/kg, I.P., BIW) (10 mg/kg, intraperitoneal injection, twice a week), the next day, the MC38 cells resuspended in PBS was inoculated subcutaneously on the right side of B-hIL2Rα humanized mice at a concentration of $5 \times 10^5$ cells/0.1 mL with 0.1 mL/mouse. The tumor volume and animal body weight were measured twice per week, and the measurement values were recorded, tumor volume (mm$^3$)=0.5×long diameter×short diameter$^2$. The results are shown in FIG. 7A and FIG. 7B and Table 12 and Table 13.

Figure 7A:
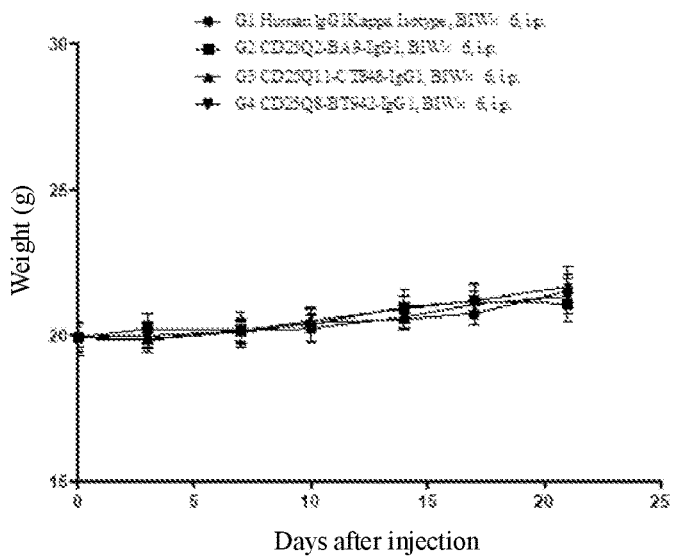

As shown in FIG. 7A, the body weight of mice increased steadily, which indicates that CD25Q2-BA9-IgG1, CD25Q8-BT942-IgG1 and CD25Q11-CT848-IgG1 (10 mg/kg, IP, BIW) do not have toxic and side effects on the mice.

Figure 7B:
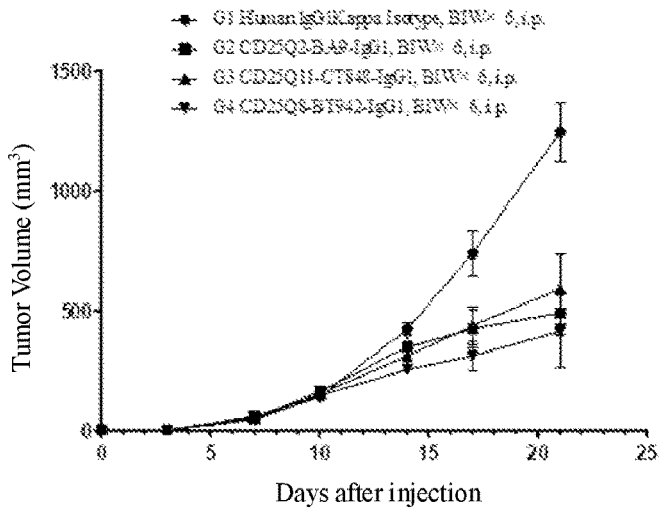

As shown in FIG. 7B, compared with the control group, CD25Q2-BA9-IgG1, CD25Q8-BT942-IgG1 and CD25Q11-CT848-IgG1 can significantly inhibit the growth of tumor of mouse MC38, of which CD25Q8-BT942-IgG1 shows a better anti-tumor effect.

TABLE 12

Data of body weight of MC38 tumor model mice (corresponding to FIG. 7A)

| Group | | Days after grouping (days) | | | | | | |
|---|---|---|---|---|---|---|---|---|
| | | 0 | 3 | 7 | 10 | 14 | 17 | 21 |
| G1 Human IgG1 Kappa Isotype | Mouse body weight (g) | 20.0 ± 0.3 | 19.9 ± 0.3 | 20.2 ± 0.3 | 20.5 ± 0.3 | 20.6 ± 0.3 | 20.8 ± 0.4 | 21.6 ± 0.6 |
| G2 CD25Q2-BA9-IgG1 | Mouse body weight (g) | 20.0 ± 0.5 | 20.3 ± 0.5 | 20.2 ± 0.6 | 20.4 ± 0.6 | 21.0 ± 0.6 | 21.2 ± 0.6 | 21.1 ± 0.6 |
| G3 CD25Q11-CT848-IgG1 | Mouse body weight (g) | 19.9 ± 0.6 | 19.9 ± 0.5 | 20.2 ± 0.4 | 20.5 ± 0.4 | 21.0 ± 0.4 | 21.2 ± 0.6 | 21.7 ± 0.7 |
| G4 CD25Q8-BT942-IgG1 | Mouse body weight (g) | 20.0 ± 0.5 | 20.0 ± 0.5 | 20.2 ± 0.4 | 20.3 ± 0.5 | 20.7 ± 0.4 | 21.1 ± 0.5 | 21.4 ± 0.6 |

TABLE 13 Data of MC38 tumor volume (corresponding to FIG. 7B)

| Group | | Days after grouping (days) | | | | | | |
|---|---|---|---|---|---|---|---|---|
| | | 0 | 3 | 7 | 10 | 14 | 17 | 21 |
| G1 Human IgG1 Kappa Isotype | Tumor volume (mm$^3$) | 0 | 0 | 45 ± 4 | 141 ± 13 | 423 ± 28 | 739 ± 94 | 1245 ± 126 |
| G2 CD25Q-BA9-IgG1 | Tumor volume (mm$^3$) | 0 | 0 | 51 ± 6 | 162 ± 22 | 348 ± 51 | 425 ± 79 | 490 ± 93 |
| G3 CD25Q11-CT848-IgG1 | Tumor volume (mm$^3$) | 0 | 0 | 49 ± 3 | 152 ± 17 | 310 ± 37 | 438 ± 79 | 590 ± 148 |
| G4 CD25Q8-BT942-IgG1 | Tumor volume (mm$^3$) | 0 | 0 | 5 ± 4 | 146 ± 8 | 254 ± 19 | 310 ± 63 | 415 ± 152 |

5.2 FACS Detection of Infiltration Effect of Immune Cells on MC38 Tumor after Administration After the 5th administration of the test mice (16 days after grouping) in 5.1, 4 mice were taken from the negative control group and 3 mice were taken from each treatment group, the mice were killed and the tumor was cut up, the digestive enzyme was added therein, incubated and digested for 40 minutes at 37° C., and resuspend as a single cell suspension after filtering and washing. 25 μL of sealing and death and life dye solution and 25 of cell suspension were added to each well of a 96-well round bottom plate, mixed well and incubated in the dark for 15 mins at 4° C.; 50 μL of surface dye was added to each well, mixed well and incubated in the dark for 30 mins at 4° C.; 150 μL of FACS solution was added to each well and washed twice, 4° C., 500 g, centrifuged for 5 mins, and the supernatant was discarded; 200 μL of the fixed solution resuspended cells were added to each well, fixed for 30 mins at room temperature after being mixed well; after fixation, centrifuged at 4° C., 1400 g for 5 mins, and the supernatant was discarded; 200 μL of membrane-penetrating solution was added to each well, centrifuged at 4° C., 1400 g for 5 mins, and the supernatant was discarded; 100 μL of intracellular dye solution was added to each well, room temperature, incubated in the dark for 30 mins; 150 μL of membrane-penetrating solution was added to each well and washed twice, 1400 g, centrifuged for 5 mins, and the supernatant was discarded; the cells were resuspend with 250 μL of PBS, and the content of CD8+ cells (Teff) in CD3, the content of CD25+Foxp3+ cells (Treg) in CD3 and the content of Foxp3+ cells (Treg) in CD4 were detected on machine. The results are shown in FIG. 8A to FIG. 8C.

Figure 8A:
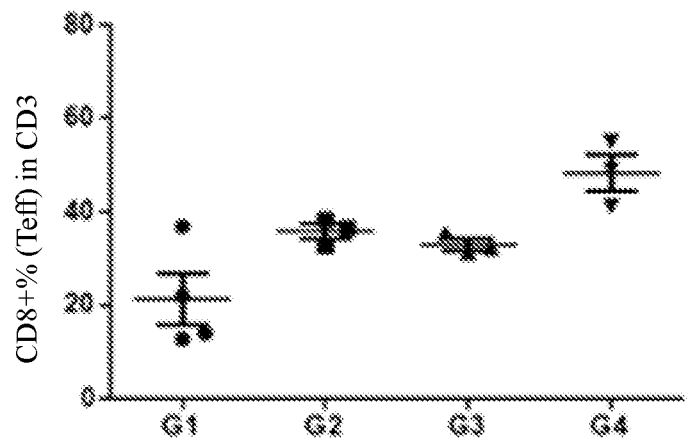
FIG. 8A shows the content of CD8+ cells (Teff) in CD3 in Example 5.2.
Figure 8B:
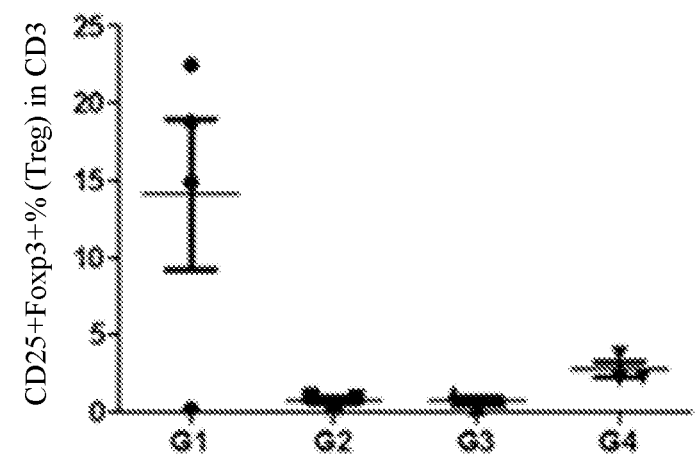
FIG. 8B shows the content of CD25+Foxp3+ cells (Treg) in CD3 in Example 5.2.
Figure 8C:
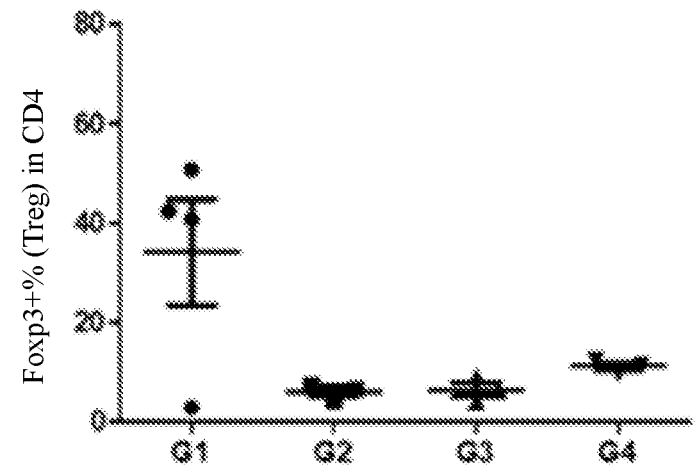
FIG. 8C shows the content of Foxp3+ cells (Treg) in CD4 in Example 5.2.

As shown in FIG. 8A to FIG. 8C, compared with the control group Human IgG1 Kappa Isotype, CD25Q2-BA9-IgG1, CD25 Q8-BT942-IgG1 and CD25Q11-CT848-IgG1 can reduce the proportion of Treg cells in tumor of mouse MC38 and increase infiltration of Teff cells, thereby improving tumor killing ability.

The invention claimed is:

1. An antibody or antigen-binding fragment thereof that binds to CD25, comprising three heavy chain complementarity determining regions (HCDR1, HCDR2 and HCDR3), wherein HCDR1 comprises SEQ ID NO: 14, HCDR2 comprises SEQ ID NO: 15, and HCDR3 comprises SEQ ID NO: 16; and three light chain complementarity determining regions (LCDR1, LCDR2 and LCDR3), wherein LCDR1 comprises SEQ ID NO: 11, LCDR2 comprises SEQ ID NO: 12, and LCDR3 comprises SEQ ID NO: 13.

2. The antibody or antigen-binding fragment thereof of claim 1, wherein the antibody or antigen-binding fragment thereof comprises a monoclonal antibody, a polyclonal antibody, a chimeric antibody, a humanized antibody, a Fab fragment, a Fab' fragment, a F(ab')2 fragment, a Fv fragment, a scFv fragment or a dsFv fragment.

3. The antibody or antigen-binding fragment thereof of claim 1, wherein the antibody or antigen-binding fragment thereof binds to human CD25.

4. A nucleic acid, wherein the nucleic acid encodes the antibody or antigen-binding fragment thereof of claim 1.

5. A cell, wherein the cell expresses the antibody or antigen-binding fragment thereof of claim 1.

6. A pharmaceutical composition, comprising the antibody or antigen-binding fragment thereof of claim 1, and a pharmaceutically acceptable carrier.

7. A method of treating or preventing-cancer, the method comprising administering the antibody or antigen-binding fragment thereof of claim 1 to a subject in need thereof.

8. The method of claim 7, wherein the cancer is selected from the group consisting of: gastric cancer, esophageal cancer, head-and-neck cancer, bladder cancer, cervical cancer, sarcoma, cytoma, lung cancer, colon cancer, ovarian cancer, renal cancer, colorectal cancer, pancreatic cancer, liver cancer, melanoma, breast cancer, myeloma, glioma, leukemia and lymphoma.

9. An antibody or antigen-binding fragment thereof that binds to CD25, comprising a heavy chain variable region with the amino acid sequence of SEQ ID NO: 4; and a light chain variable region with the amino acid sequence of SEQ ID NO: 3.

10. The antibody or antigen-binding fragment thereof of claim 9, wherein the antibody or antigen-binding fragment thereof comprises a monoclonal antibody, a polyclonal antibody, a chimeric antibody, a humanized antibody, a Fab fragment, a Fab' fragment, a F(ab')2 fragment, a Fv fragment, a scFv fragment or a dsFv fragment.

11. A nucleic acid, wherein the nucleic acid encodes the antibody or antigen-binding fragment thereof of claim 9.

12. A cell, wherein the cell expresses the antibody or antigen-binding fragment thereof of claim 9.

13. A pharmaceutical composition, comprising the antibody or antigen-binding fragment thereof of claim 9, and a pharmaceutically acceptable carrier.

14. A method of treating cancer, the method comprising administering the antibody or antigen-binding fragment thereof of claim 9 to a subject in need thereof.

* * * * *

UNITED STATES PATENT AND TRADEMARK OFFICE
CERTIFICATE OF CORRECTION

PATENT NO. : 12,325,751 B2
APPLICATION NO. : 17/601321
DATED : June 10, 2025
INVENTOR(S) : Deyong Song, Xiu Liu and Jing Han Page 1 of 1

It is certified that error appears in the above-identified patent and that said Letters Patent is hereby corrected as shown below:

In the Claims

In Column 31, Line 38, In Claim 7, delete "or preventing-cancer," and insert -- cancer, --.

Signed and Sealed this
Nineteenth Day of August, 2025

Coke Morgan Stewart
*Acting Director of the United States Patent and Trademark Office*

SEQUENCE LISTING

```
<160> NUMBER OF SEQ ID NOS: 20

<210> SEQ ID NO 1
<211> LENGTH: 107
<212> TYPE: PRT
<213> ORGANISM: Homo sapiens
<220> FEATURE:
<223> OTHER INFORMATION: BA9 VL

<400> SEQUENCE: 1

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Leu Arg Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Trp
                85                  90                  95

Thr Phe Gly Gln Gly Thr Lys Val Glu Ile Lys
            100                 105

<210> SEQ ID NO 2
<211> LENGTH: 114
<212> TYPE: PRT
<213> ORGANISM: Homo sapiens
<220> FEATURE:
<223> OTHER INFORMATION: BA9 VH

<400> SEQUENCE: 2

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Ile Tyr Asn Pro Ser Leu Lys
50                  55                  60
```

```
Ser Arg Val Thr Ile Ser Leu Asp Thr Ser Lys Asn Gln Phe Ser Leu
 65                  70                  75                  80

Lys Leu Ser Ser Val Thr Ala Ala Asp Thr Ala Leu Tyr Tyr Cys Ala
                 85                  90                  95

Arg Gly Glu Ala Phe Asp Ile Trp Gly Gln Gly Thr Met Val Thr Val
            100                 105                 110

Ser Ser
```

<210> SEQ ID NO 3
<211> LENGTH: 113
<212> TYPE: PRT
<213> ORGANISM: Homo sapiens
<220> FEATURE:
<223> OTHER INFORMATION: BT942 VL

<400> SEQUENCE: 3

```
Asp Ile Gln Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Tyr Thr Phe Gly Gln Gly Thr Lys Val Glu Ile
            100                 105                 110

Lys
```

<210> SEQ ID NO 4
<211> LENGTH: 122
<212> TYPE: PRT
<213> ORGANISM: Homo sapiens
<220> FEATURE:
<223> OTHER INFORMATION: BT942 VH

<400> SEQUENCE: 4

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Asp
                 20                  25                  30

Ala Ile Asn Trp Val Arg Gln Ala Pro Gly Gln Gly Leu Glu Trp Met
             35                  40                  45

Gly Arg Ile Ile Pro Ile Phe Gly Val Ala Asp Tyr Ala Gln Lys Phe
 50                  55                  60

Gln Gly Arg Val Thr Leu Thr Ala Asp Lys Ser Thr Ser Thr Ala Tyr
 65                  70                  75                  80

Met Asp Leu Ser Ser Leu Arg Ser Glu Asp Thr Ala Val Phe Tyr Cys
                 85                  90                  95

Ala Arg Glu Arg Gly Asp Tyr Ser Asn Phe Trp Tyr Phe Asp Leu Trp
            100                 105                 110

Gly Arg Gly Thr Leu Val Thr Val Ser Ser
            115                 120
```

```
<210> SEQ ID NO 5
<211> LENGTH: 6
<212> TYPE: PRT
<213> ORGANISM: Homo sapiens
<220> FEATURE:
<223> OTHER INFORMATION: BA9 LCDR1

<400> SEQUENCE: 5

Gln Ser Leu Arg Ser Tyr
1               5

<210> SEQ ID NO 6
<211> LENGTH: 3
<212> TYPE: PRT
<213> ORGANISM: Homo sapiens
<220> FEATURE:
<223> OTHER INFORMATION: BA9 LCDR2

<400> SEQUENCE: 6

Lys Ala Ser
1

<210> SEQ ID NO 7
<211> LENGTH: 9
<212> TYPE: PRT
<213> ORGANISM: Homo sapiens
<220> FEATURE:
<223> OTHER INFORMATION: BA9 LCDR3

<400> SEQUENCE: 7

Gln Gln Tyr Asn Ser Tyr Ser Trp Thr
1               5

<210> SEQ ID NO 8
<211> LENGTH: 8
<212> TYPE: PRT
<213> ORGANISM: Homo sapiens
<220> FEATURE:
<223> OTHER INFORMATION: BA9 HCDR1

<400> SEQUENCE: 8

Gly Gly Ser Phe Ser Gly Tyr Tyr
1               5

<210> SEQ ID NO 9
<211> LENGTH: 7
<212> TYPE: PRT
<213> ORGANISM: Homo sapiens
<220> FEATURE:
<223> OTHER INFORMATION: BA9 HCDR2

<400> SEQUENCE: 9

Ile Asp His Ser Gly Ser Thr
1               5

<210> SEQ ID NO 10
<211> LENGTH: 8
<212> TYPE: PRT
<213> ORGANISM: Homo sapiens
<220> FEATURE:
<223> OTHER INFORMATION: BA9 HCDR3

<400> SEQUENCE: 10

Ala Arg Gly Glu Ala Phe Asp Ile
1               5
```

```
<210> SEQ ID NO 11
<211> LENGTH: 12
<212> TYPE: PRT
<213> ORGANISM: Homo sapiens
<220> FEATURE:
<223> OTHER INFORMATION: BT942 LCDR1

<400> SEQUENCE: 11

Gln Ser Val Leu Tyr Ser Ser Asn Asn Lys Asn Tyr
1               5                   10

<210> SEQ ID NO 12
<211> LENGTH: 3
<212> TYPE: PRT
<213> ORGANISM: Homo sapiens
<220> FEATURE:
<223> OTHER INFORMATION: BT942 LCDR2

<400> SEQUENCE: 12

Trp Ala Ser
1

<210> SEQ ID NO 13
<211> LENGTH: 9
<212> TYPE: PRT
<213> ORGANISM: Homo sapiens
<220> FEATURE:
<223> OTHER INFORMATION: BT942 LCDR3

<400> SEQUENCE: 13

Gln Gln Tyr Tyr Ser Thr Pro Tyr Thr
1               5

<210> SEQ ID NO 14
<211> LENGTH: 8
<212> TYPE: PRT
<213> ORGANISM: Homo sapiens
<220> FEATURE:
<223> OTHER INFORMATION: BT942 HCDR1

<400> SEQUENCE: 14

Gly Gly Thr Phe Ser Ser Asp Ala
1               5

<210> SEQ ID NO 15
<211> LENGTH: 8
<212> TYPE: PRT
<213> ORGANISM: Homo sapiens
<220> FEATURE:
<223> OTHER INFORMATION: BT942 HCDR2

<400> SEQUENCE: 15

Ile Ile Pro Ile Phe Gly Val Ala
1               5

<210> SEQ ID NO 16
<211> LENGTH: 15
<212> TYPE: PRT
<213> ORGANISM: Homo sapiens
<220> FEATURE:
<223> OTHER INFORMATION: BT942 HCDR3

<400> SEQUENCE: 16

Ala Arg Glu Arg Gly Asp Tyr Ser Asn Phe Trp Tyr Phe Asp Leu
1               5                   10                  15

<210> SEQ ID NO 17
```

```
<211> LENGTH: 330
<212> TYPE: PRT
<213> ORGANISM: Homo sapiens
<220> FEATURE:
<223> OTHER INFORMATION: heavy chain constant region

<400> SEQUENCE: 17
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

```
<210> SEQ ID NO 18
<211> LENGTH: 119
<212> TYPE: PRT
<213> ORGANISM: Homo sapiens
<220> FEATURE:
<223> OTHER INFORMATION: MA251 VH
```

-continued

<400> SEQUENCE: 18

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Ile Gln Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Ala Tyr Gly Tyr Asp Gly Ser Trp Leu Ala Tyr Trp Gly Gln Gly
            100                 105                 110

Thr Leu Val Thr Val Ser Ser
        115

<210> SEQ ID NO 19
<211> LENGTH: 106
<212> TYPE: PRT
<213> ORGANISM: Homo sapiens
<220> FEATURE:
<223> OTHER INFORMATION: MA251 VL

<400> SEQUENCE: 19

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Phe
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Asn Arg Val Glu Ala Glu
65                  70                  75                  80

Asp Ala Asp Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 20
<211> LENGTH: 107
<212> TYPE: PRT
<213> ORGANISM: Homo sapiens
<220> FEATURE:
<223> OTHER INFORMATION: light chain constant region

<400> SEQUENCE: 20

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

-continued

```
Thr Tyr Ser Leu Ser Ser Thr Leu Thr Leu Ser Lys Ala Asp Tyr Glu
65              70              75                  80

Lys His Lys Val Tyr Ala Cys Glu Val Thr His Gln Gly Leu Ser Ser
            85              90                  95

Pro Val Thr Lys Ser Phe Asn Arg Gly Glu Cys
            100             105
```